United States Patent [19]

Mandl

[11] Patent Number: 5,898,304
[45] Date of Patent: Apr. 27, 1999

[54] SENSOR ARRANGEMENT INCLUDING A NEURAL NETWORK AND DETECTION METHOD USING SAME

[75] Inventor: Roland Mandl, Ortenburg, Germany

[73] Assignee: Micro-Epsilon Messtechnik GmbH & Co. KG, Ortenburg, Germany

[21] Appl. No.: 08/809,036

[22] PCT Filed: Sep. 21, 1995

[86] PCT No.: PCT/DE95/01296

§ 371 Date: Mar. 21, 1997

§ 102(e) Date: Mar. 21, 1997

[87] PCT Pub. No.: WO96/09516

PCT Pub. Date: Mar. 28, 1996

[30] Foreign Application Priority Data

Sep. 22, 1994 [DE] Germany .............................. 44 33 772

[51] Int. Cl.$^6$ ............................. G01B 7/06; G01N 27/90; G01R 33/12; G06F 19/00
[52] U.S. Cl. .................... 324/232; 324/202; 324/207.16; 324/225; 324/230; 324/234; 324/607; 702/38; 702/85; 702/170; 702/189
[58] Field of Search ............................... 324/202, 207.12, 324/207.16, 207.26, 225–226, 229–234, 236–238, 605, 607; 702/38, 57, 64, 85, 166, 170, 189

[56] References Cited

U.S. PATENT DOCUMENTS

| 4,084,136 | 4/1978 | Libby et al. ............................. 324/238 |
| 4,263,551 | 4/1981 | Gregory et al. ......................... 324/233 |
| 5,055,784 | 10/1991 | Jaeger et al. ............................ 324/233 |

FOREIGN PATENT DOCUMENTS 42 01 502  7/1993  Germany .

OTHER PUBLICATIONS

Patent Abstracts of Japan, vol. 13, No. 210 (P–872), May 17, 1989 for "Shape Detector".

Patent Abstracts of Japan, vol. 15, No. 79 (P–1170), Feb. 25, 1991 for "AC–Loss Measuring Apparatus".

Patent Abstracts of Japan, vol. 12, No. 266 (P–735), Jul. 26, 1988 for "Nondestructive Measuring Method for Tube Thickness".

Patent Abstracts of Japan, vol. 5, No. 32 (P–050), Feb. 27, 1981 for "Device for Measuring Magnetic Permeability".

*Materials Evaluation*, "Eddy Current Defect Characterization Using Neural Networks", vol. 48, Mar. 1990, pp. 342–347.

SICE '93, "Neural Network Based Sensor Integration for On–Line Weld Quality Control"; pp. 1483–1486.

*Primary Examiner*—Gerard Strecker
*Attorney, Agent, or Firm*—Alston & Bird LLP

[57] ABSTRACT

A sensor arrangement (1) comprising at least one measuring coil (2), at least one voltage source (3) for the measuring coil (2), and an evaluation unit (4) with means for detecting, processing, and evaluating measured signals. This sensor arrangement (1) is used to measure distances and thicknesses substantially independently of the material involved, without the user having to know the physicomathematical relations between the influencing quantities and the measured values. In order to evaluate the measured signals, the evaluation unit (4) of the sensor arrangement comprises a neural network (5) with an input layer, at least one hidden layer, an output layer, and connection weights for the individual layers. The connection weights are determined and stored in a learning phase by measurements taken on a plurality of different suitable learning objects with known actual values.

18 Claims, 5 Drawing Sheets

SENSOR ARRANGEMENT INCLUDING A NEURAL NETWORK AND DETECTION METHOD USING SAME

FIELD OF THE INVENTION

The invention relates to a sensor arrangement comprising at least one measuring coil, at least one source of voltage for the measuring coil, and an evaluation unit with means for detecting, processing, and evaluating measured signals.

BACKGROUND OF THE INVENTION

Such sensor arrangements, for example with eddy-current sensors having a measuring coil, have been used for years for a large variety of measurements, such as, for example, for measuring the distance to an object, for measuring the thickness of a coating layer on an object, for measuring the conductivity and magnetic. permeability of a target, or for examining the homogeneity, and for detecting damage in the structure of the target surface. Normally, measurements with the known sensor arrangements require an extensive knowledge of physical relations between quantity being determined, the measured value, and possible disturbance variables. This knowledge must often be converted to measuring and evaluation electronics that are specially adapted to the measuring problem. Some measurements cannot be carried out at all, since different influence variables superpose, so that no clear statement of the measurements is obtained. When measuring the thickness of a conductive layer on a likewise conductive carrier with a known sensor arrangement, measuring errors will occur, for example, despite an adaptation to the particular target material. This applies, for example, to the existence of local inhomogeneities, magnetization, conductivity, effective permeability, temperature gradients, etc. When using known sensor arrangements of the state of the art, it will be necessary to find again for each measuring problem the mathematical relations between influence variables and measured values. The mathematical relations are in part complex and extremely nonlinear, so that this procedure, if possible at all, will take an enormous amount of time.

The complexity of the mathematical relations between influence variables and measured values is to be demonstrated by the example of the noncontacting distance measurement by the eddy-current principle. The impedance of a coil (real part and imaginary part) varies upon approaching an electrically and/or magnetically conductive object. Thus, by measuring the impedance of a measuring coil, it is possible to determine the distance between the coil and the object being measured. In the object being measured, a current is induced, which counteracts the excitation of the coil. This reaction is again dependent on the electric conductivity and on the magnetic behavior of the measuring object, namely the material parameters. Same are again temperature-dependent. Furthermore, the impedance values are frequency-dependent, and nonlinearly related to the measuring distance. Reliable results of the measurement may be obtained only when all these influence variables are considered.

SUMMARY OF THE INVENTION

It is now the object of the invention to describe a sensor arrangement of the kind under discussion, which permits the user to perform largely material-independent measurements, without knowledge of the mathematical background.

The sensor arrangement of the present invention accomplishes the foregoing object by providing a characteristic features of claim 1. Accordingly, providing a sensor arrangement which is configured such that the evaluation unit for evaluating the measured signals comprises a neural network of neurons or nodes arranged into layers including an input layer, at least one hidden layer, and an output layer, and connection weights for the nodes of the individual layers, and that the connection weights are determined and stored during a learning phase by measuring the outputs of the network produced when a plurality of different suitable learning objects with known actual values are input to the network, and using an algorithm to arrive at connection weights which produce the known actual values as outputs of the network.

In accordance with the invention, it has been recognized that a detailed knowledge of the physicomathematical relations between disturbance variables and measured values is no longer needed, when a suitably trained neural network is used for the evaluation of the measured signals. It has further been recognized that the neural network of a sensor arrangement can also be trained for different kinds of measurements by a suitable selection of the learning objects and measurements in the learning phase. Therefore, the sensor arrangement of the present invention is capable of performing different kinds of measurements. Furthermore, it has been recognized that the suitable optimal selection of different learning objects also permits measurements of unknown measuring objects. The neural network in use approximates the relations such that it is also possible to determine correctly actual values that are between the learning points. A linearization or calibration as is common in conventional systems is thus no longer necessary.

In the case of the noncontacting distance measurement, it is possible to eliminate the different influences of different materials in that during the learning phase measurements are performed on learning objects consisting of different suitable materials. If the actual measurements are to be made, for example on metallic materials, likewise metallic objects will be used for the learning phase by selecting, for example, learning objects of aluminum, iron, stainless steel, etc. These measurements supply input variables for the neural network, which assist in determining the connection weights of the neural network, since the actual values of the learning objects are known. In this connection, the system of equations for the connection weights is possibly repeatedly overdefined. In this case, a mean-square approximation is performed. Underdefined systems of equations or heavily correlated input values result in a lack of learning success. After the learning phase, the determined connection weights are held in a corresponding electronic element. The connection weights permit forwarding a mapping instruction of the input vector of input values to one or more output values. Thus, the neural network finds an approximation for a relation that cannot be solved in mathematically closed manner. In the measuring phase, this facilitates distance measurements also on measuring objects, which consist of a different material than any of the learning objects.

In an advantageous embodiment of the sensor arrangement in accordance with the invention, a back-propagation network is used as neural network. Such network structures are already adequately known from the literature, so that it is not necessary to describe in more detail a concrete configuration of a back-propagation network. It should only be remarked that a back-propagation network has a network structure without feedback.

There exist various possibilities of realizing such a network. Satisfactory results were obtained with a single-stage network structure, which has only one hidden layer. For example, different types of a single-stage network structure which yielded satisfactory results include:

Type 1: eight input nodes, five nodes in the hidden layer, and one output node;

Type 2: eight input nodes, one node in the hidden layer, and one output node;

Type 3: six input nodes, five nodes in the hidden layer, and one output node;

Type 4: four input nodes, four nodes in the hidden layer, and one output node;

Type 5: two input nodes, two nodes in the hidden layer, and one output node.

Possible, however, is also a two-stage network structure with two hidden layers.

In a particularly advantageous embodiment of the sensor arrangement in accordance with the invention, a strictly monotonic and differentiable sigmoid function, which is adapted to the nonlinearity behavior of the measuring coil, is used as transfer function of the elements of a backpropagation network. Although there occurs an individual adaptation of the transfer function—and, thus, of the neural network—to the physical conditions of the measuring coil, the advantages of a sigmoid curve shape are however maintained. Any arbitrary input value is mapped to the interval between 0 and 1. Furthermore, input values which are close to 0, are spread apart to a greater extent and, thus, are better separated by the slope of the curve in this range. Very high positive or negative values lead always to activities near 1 and respectively near 0. Their absolute magnitude is relatively irrelevant as a result of the very flat curve shape in these ranges. The sigmoid function has also the advantage that its differentiation is very simple.

Preferably, the source of voltage is followed by a mixer arrangement, which generates selectively energizing voltages of different amplitude and frequency. These measurements of the impedance of the measuring coil at different frequencies represent a possibility of realizing uncorrelated, but physicomathematically connected input values for the neural network.

To obtain now linearly independent measured values for input to the neural network, it is proposed to use as a component of the evaluation unit a four-wire-type circuit arrangement, which comprises one leg for detecting the voltage curve and another leg for detecting the current flow of the measuring coil. Both signals are also processed in the evaluation unit, in that they undergo an A-D conversion and complex division. In this manner, a complex impedance value is determined, which is independent of the amplitude and the phase of the energizing voltage. The evaluation unit may further comprise means for normalizing and scaling the measured signals. Only then are the thus-determined impedance values supplied as input values to the neural network.

Furthermore, the present invention relates to a method of detecting measured values with a sensor arrangement of the present invention. This method is intended to provide the user of the sensor arrangement in accordance with the invention with an automatism which permits the user to carry out different kinds of measurements without knowledge of the mathematical background.

To this end, the detection of measured values must be performed such that for actual values that are to be determined, as many nonlinearly related, namely uncorrelated, but physicomathematically connected input values are determined for the neural network as there are input nodes. It has been recognized that, at different measuring frequencies, the impedance values of the measuring coil fulfill the requirements of the input values for neural networks. Therefore, in the measuring phase, the impedance values of the measuring coil are determined at different frequencies and applied accordingly normalized to the input of the neural network. To this end, the voltage curve and current flow are detected on the measuring coil at different frequencies.

There exist various possibilities of determining the spectra of the digitized voltage curve and of the digitized current flow. In a particularly advantageous application of the method, the spectra of the digitized voltage curve and of the digitized current flow are determined by iteration with the use of a spectral estimator. In this connection, the spectrum is determined as $$x_{n+1}\text{HfL}:=x_n\text{HfL}\frac{1}{kn+1}\sum xp^{a\pi T}T_0^N + \frac{1}{k} - \frac{1}{kn+1}\sum x_n\text{HfL}$$

where $x_n(t)$ is the sampling value at the time n, $X_n(f)$ the spectrum at the time n, and $X_{n+1}(f)$ the newly calculated spectrum at the time n+1. With the term $aT/T_0$ the desired spectral line is selected. As starting value of the iteration, one uses n=0, and $X_0(f)=0$. $X(f)$ is a complex quantity, $X(t)$ is real. For $nT=T_0$ (one period duration), the result corresponds exactly to that of a discrete Fourier transform. This applies likewise to integral multiples of a period. Thus, the method represents a spectral estimator.

In a particularly advantageous variant of the method in accordance with the invention, a special square-wave voltage is used as energizing voltage for the measuring coil. The spectral proportion of higher harmonics drops in a pure square-wave voltage as the frequency increases. This is compensated by adding three additional square-wave signals of a lesser amplitude for the first four spectral lines. Such a compensation is advantageous, since the attainable resolution of the A-D converter is the same for all used frequencies, and in this manner it is possible to realize an optimal modulation of a high dynamic. Thus the square-wave voltage is advantageously formed by a periodically recurrent sequence of respectively one square pulse of a larger amplitude and three square pulses of a smaller amplitude.

Furthermore, it will be advantageous, when the alternating energizing voltage of the measuring coil is superposed by a direct current component. The measured current facilitates conclusions as to the temperature of the measuring coil. The pure ohmic component of the coil impedance may be supplied to the neural network as additional input value, which achieves in a simple manner a temperature compensation of the sensor.

Advantageously, the sensor arrangement of the present invention as well as the above-described method of detecting measured values with the sensor arrangement of the invention may be used for measuring distance and coating thickness. Thus, for example, it is possible to determine the thickness of metal foils or even the thickness of coatings. A further advantageous use of the sensor arrangement in accordance with the invention is the measurement of electric conductivity and effective permeability of surface coatings.

BRIEF DESCRIPTION OF THE DRAWINGS

The are various possibilities of improving and further developing in advantageous manner the teaching of the present invention. To this end reference is made to the following description of an embodiment of the invention with reference to the drawing. In conjunction with the description of the preferred embodiment of the invention with reference to the drawing, also generally preferred embodiments and further developments of the teaching are described. In the drawing.

DETAILED DESCRIPTION OF PREFERRED EMBODIMENTS

Figure 1:
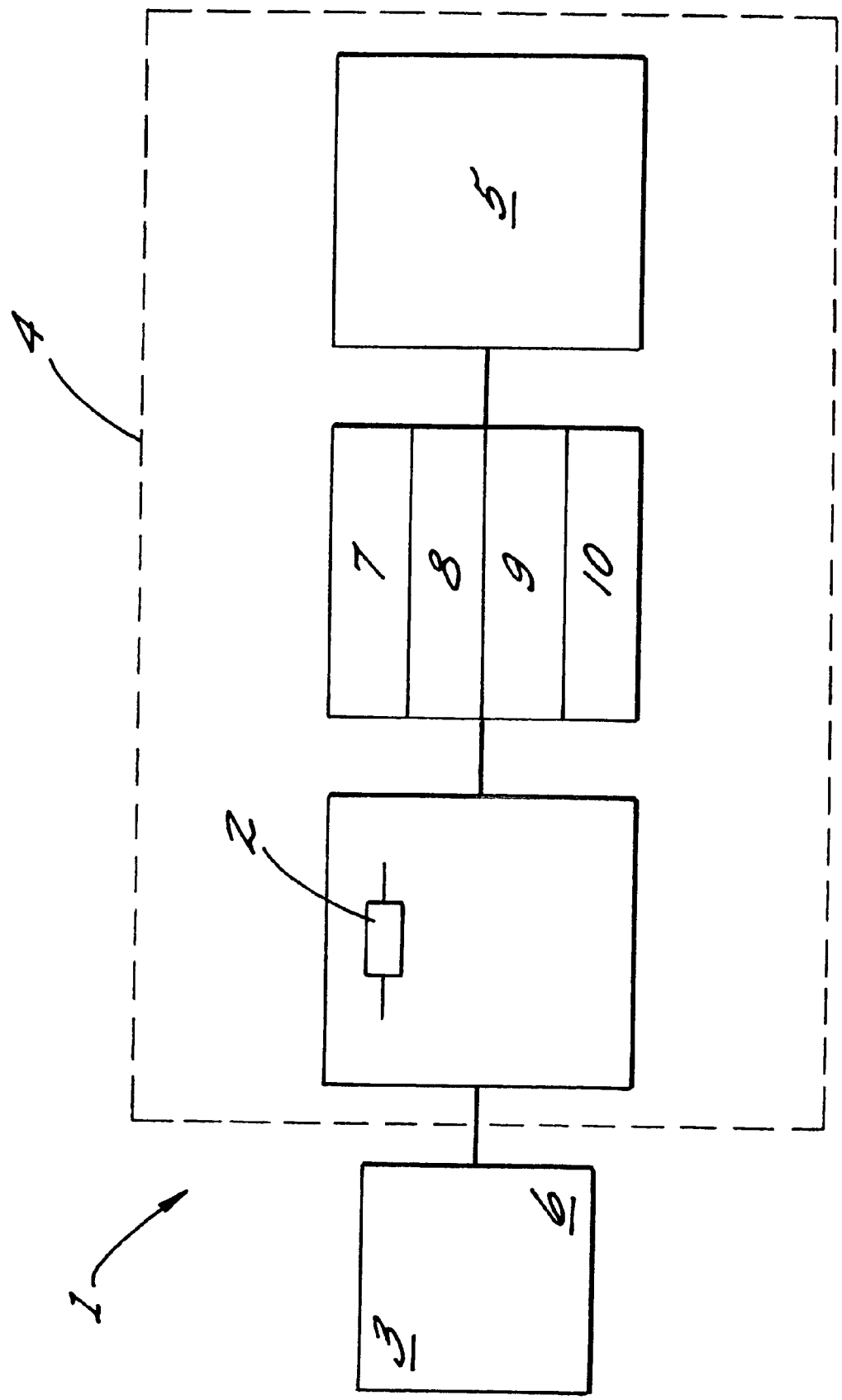
FIG. 1 is a block diagram illustrating the schematic layout of a sensor arrangement in accordance with the invention.

Shown in FIG. 1 is a basic layout of a sensor arrangement 1 in accordance with the invention. The sensor arrangement 1 comprises a measuring coil 2 as sensor element and a source of voltage 3 for the measuring coil 2. Further provided is an evaluation unit 4, which comprises means for detecting, processing, and evaluating measured signals.

In accordance with the invention, the means for evaluating measured signals is a neural network 5 with an input layer, at least one hidden layer, an output layer, and connection weights for the individual layers. The connection weights are determined and stored in a learning phase by measurements on a plurality of different, suitable learning objects each with a known actual value.

The illustrated neural network 5 is a back-propagation network with a single-stage network structure, i.e., the network structure has only one hidden layer. The input layer of the neural network has, for example, eight input nodes, whereas the hidden layer has five nodes, and the output layer is formed by a single output node. Used as transfer function of the neural network 5 is a sigmoid function adapted to the nonlinearity behavior of measuring coil 2 and having a strictly monotonic and differentiable curve.

Figure 2:
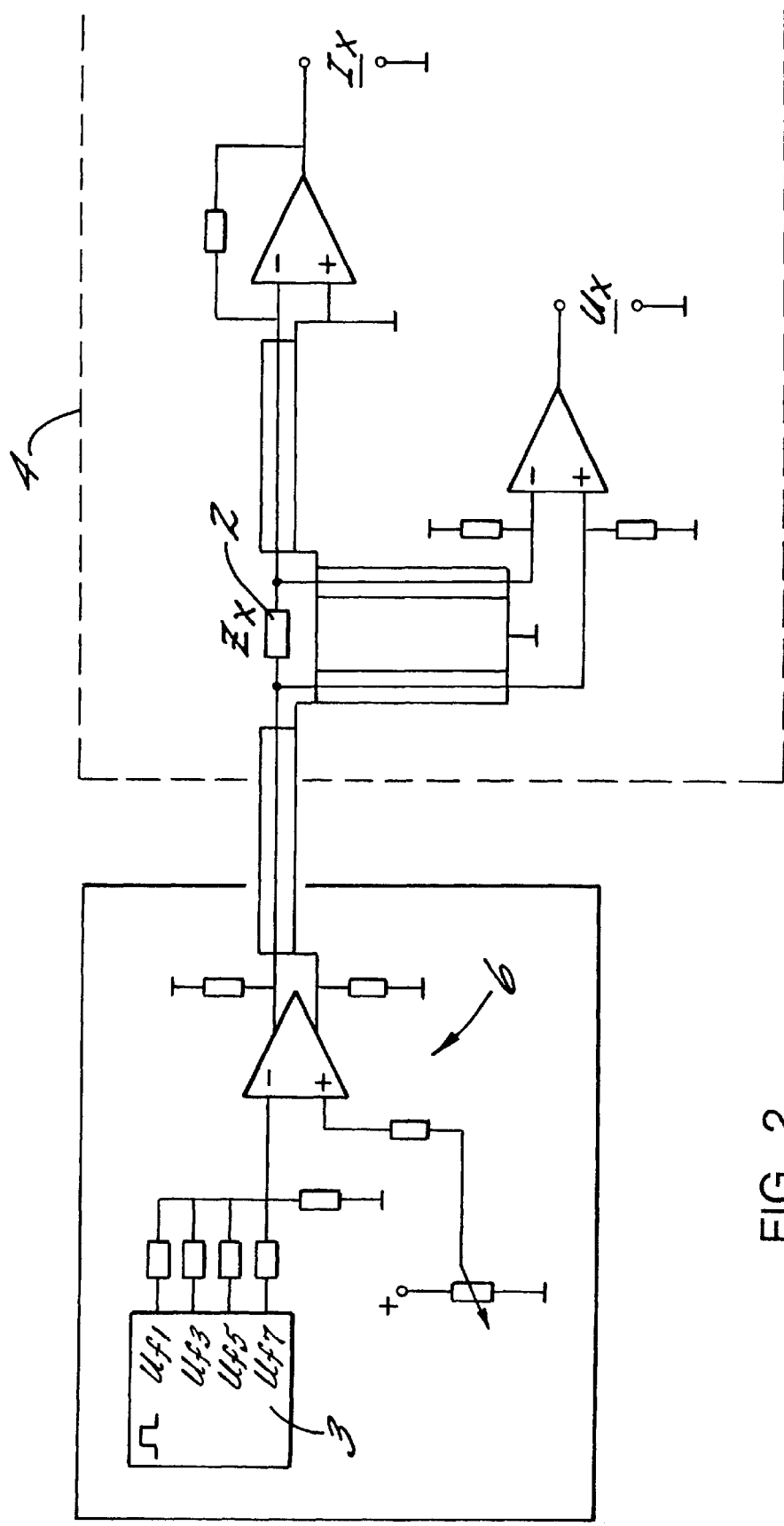
FIG. 2 is a circuit diagram for energizing a measuring coil as well as for detecting measured signals on the measuring coil within the scope of a sensor arrangement in accordance with the invention.
Figure 3:
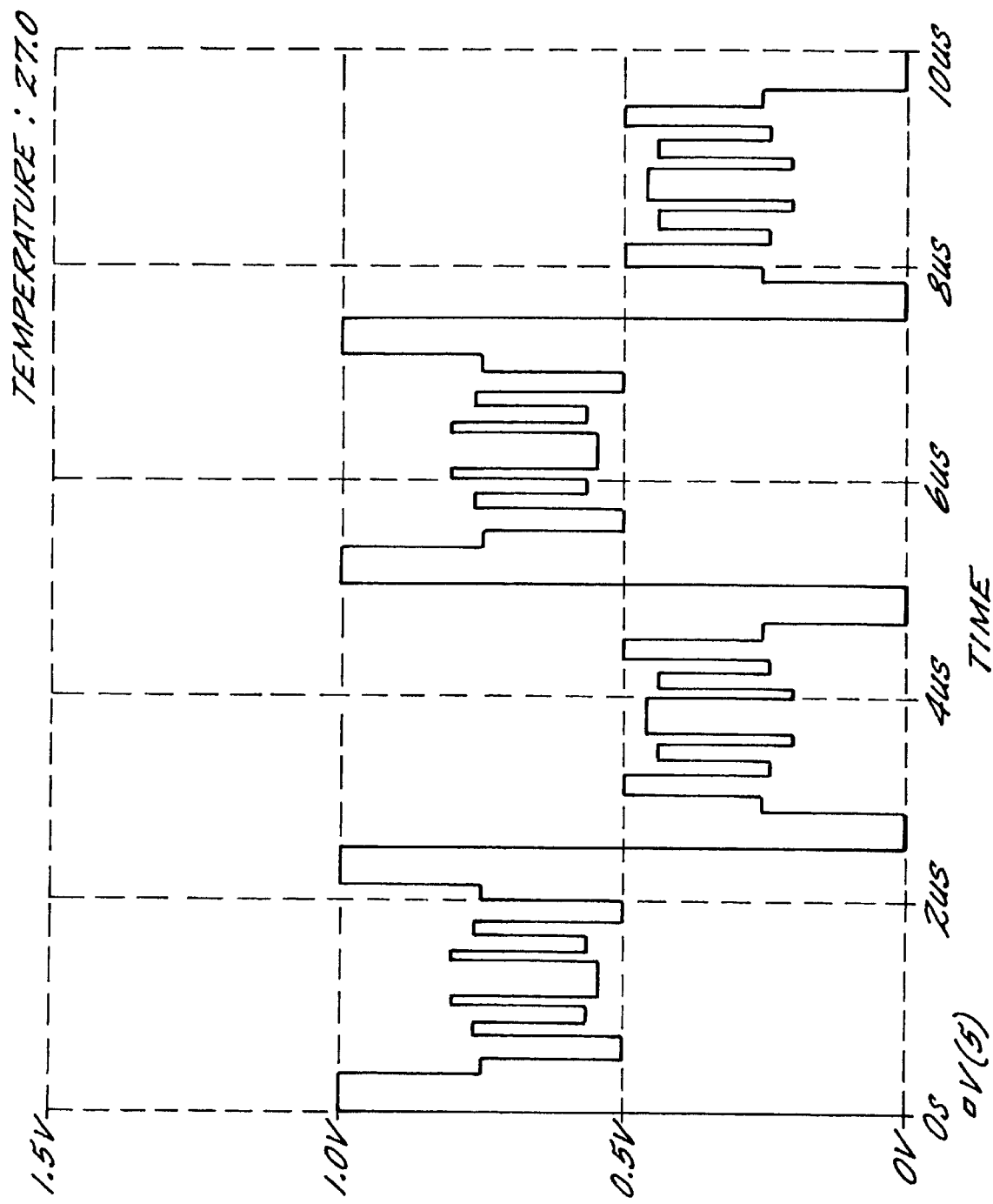
FIG. 3 is a signal curve of the energizing voltage of the measuring coil.
Figure 4:
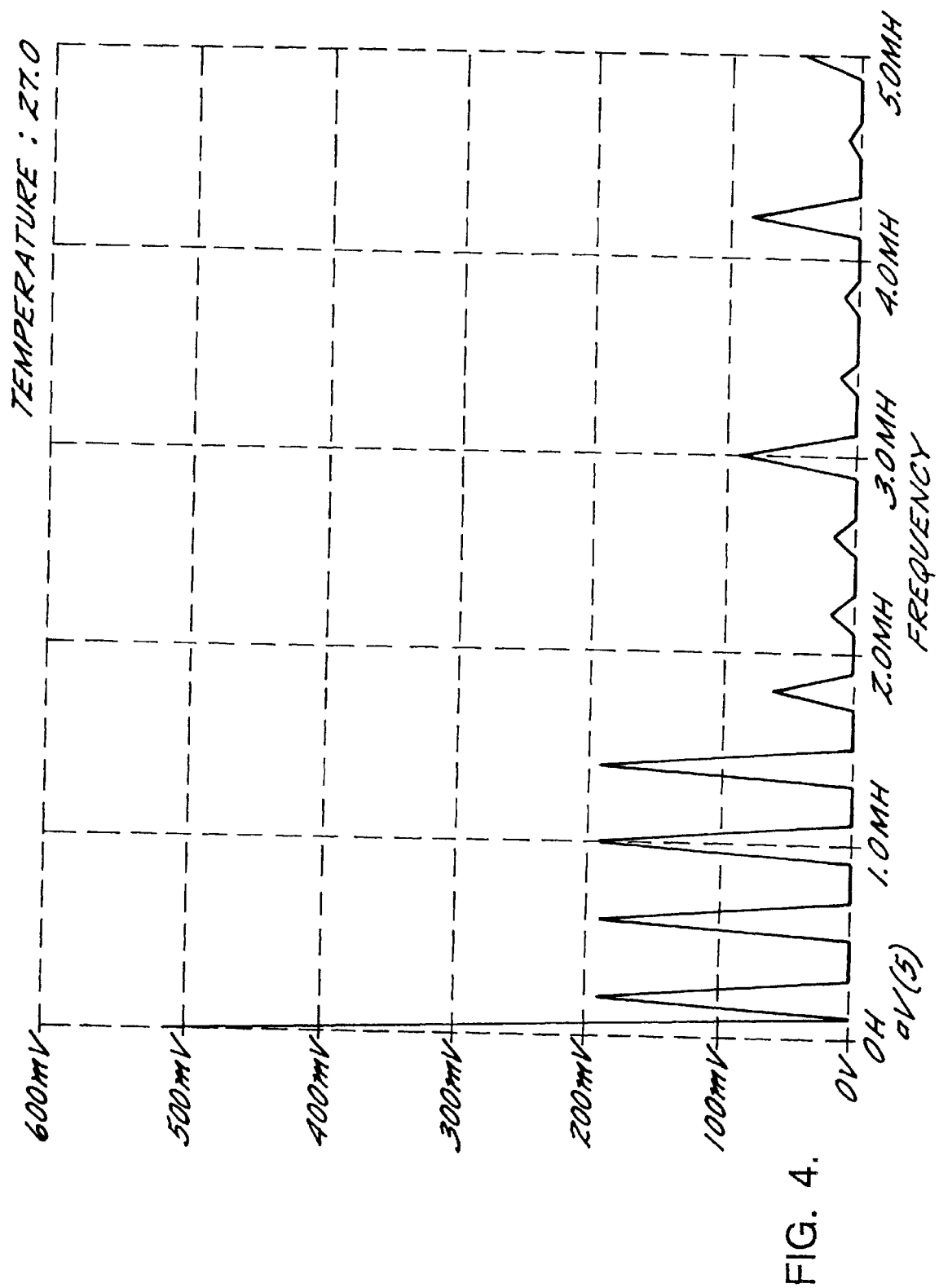
FIG. 4 is a graph of the energizing voltage of FIG. 3 in its frequency range.

A possibility of realizing voltage source 3, measuring coil 2, and the means for detecting the measured signals within the scope of evaluation unit 4 is shown in FIG. 2. The actual voltage source 3 is followed by a mixer arrangement 6, which generate selectively energizing voltages of different amplitudes and frequencies. The illustrated mixer arrangement 6 facilitates realization of an energizing voltage in the form of a square-wave signal, which is formed by a periodically recurrent sequence of respectively one square pulse of a larger amplitude and three square pulses of a smaller amplitude. Such a signal curve is shown in FIG. 3. The associated graph in the frequency range may be noted from FIG. 4. As best seen in FIG. 4, a signal with four substantially equally strong frequency components is generated by adding several square pulses of smaller amplitudes to a square pulse of a larger amplitude.

As a result of energizing the measuring coil 4 with such a square signal, it is possible to determine the impedance values of measuring coil 2 at these four different frequencies.

Shown in FIG. 2 is that portion of the evaluation unit 4, which detects the measured signals, namely the voltage curve $U_x$ and the current flow $I_x$ on measuring coil 2. The voltage curve is detected parallel to the measuring coil 2, whereas the current flow is detected serial to the measuring coil 2. This circuit arrangement is realized by the four-wire circuit method, wherein the individual current branches are shielded.

Both the voltage signal and the current signal undergo an A-D conversion and complex division. In this process, uncorrelated impedance values of measuring coil 2 result at the different frequencies, which are independent of the amplitude and phase of the energizing voltage.

The circuit shown in FIG. 2 is followed by processing means, which form likewise a part of evaluation unit 4. More specifically, they include means for digitizing, namely an A-D converter 7, means for carrying out a Fourier analysis for voltage and current 8, means for complex dividing at different frequencies 9, and finally means for complex normalizing and scaling 10. Only next to these signal processing stages are the input nodes of the neural network 5, as shown in FIG. 1.

Figure 5:
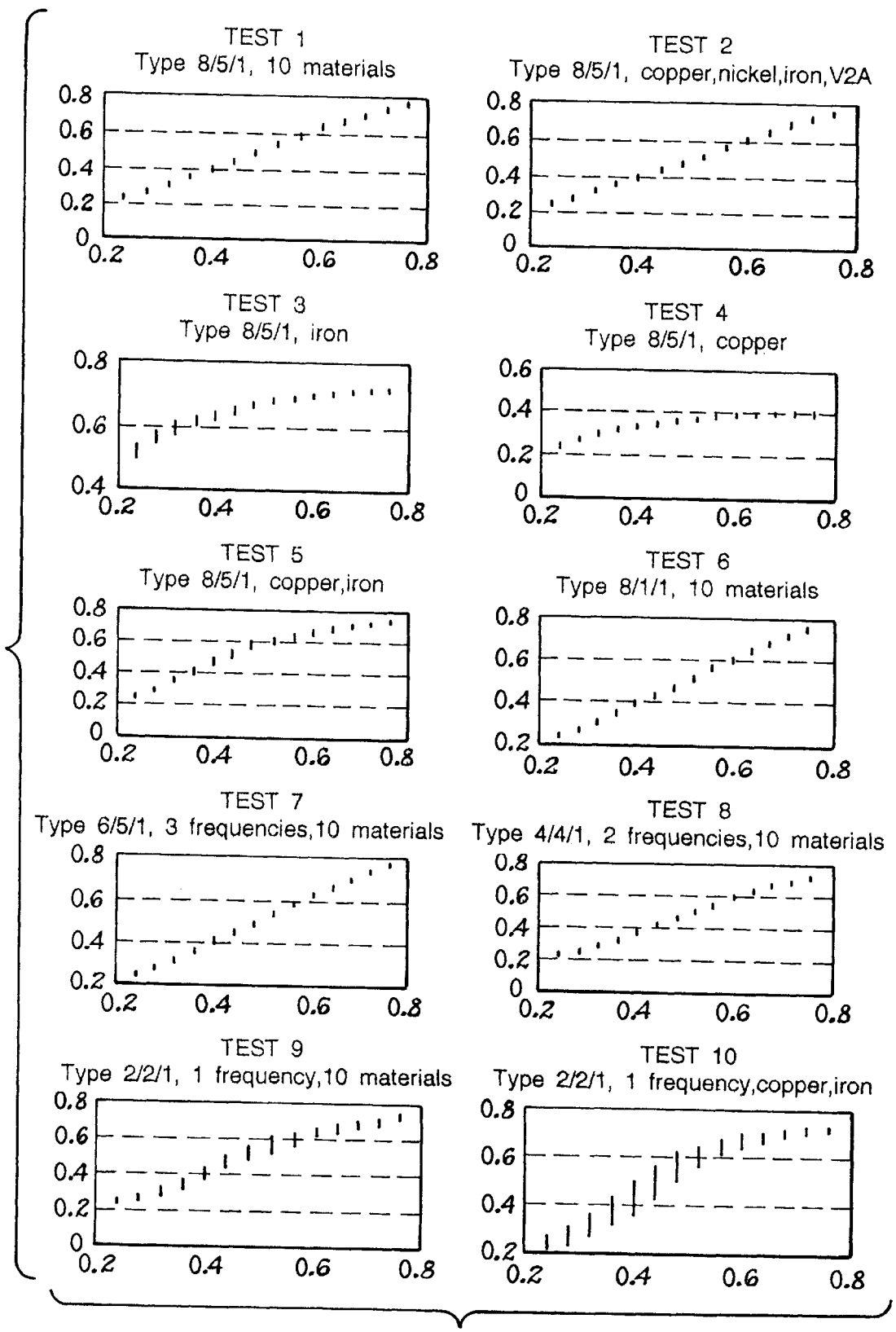
FIG. 5 illustrates test results of measurements made on metals with unknown material parameters.

In FIG. 5, the headings of the test diagrams of distance measurements are to be interpreted as follows:

In all ten tests single-stage neural networks were used, which have only one hidden layer. Type 8/5/1 indicates a network structure with eight input nodes, five nodes in the hidden layer, and one output node. Indicated next thereto are the materials used during the training, such as, for example, copper, iron, or V2A steel. The test was always conducted with ten different metals. The two axes correspond to the desired distance or the distance estimated by the network. Starting with test 7, the number of used measuring frequencies was reduced. As can be noted, effective of at least two frequencies, usable results are obtained by the method, this means a good correlation between the actual distance and the detected distance. However, for a higher number of measuring frequencies, a better approximation quality will result.

As a whole, the following statements can be made:

The material properties of metals, which have not been learning objects are correctly recognized and are interpolated or extrapolated. This allows to shorten the calibrating operation significantly.

The classification algorithm of the learning phase determines the material parameters, for example, conductivity and effective permeability of the material, and it compensates for their influence on the distance measurement.

Material parameter fluctuations caused by temperature changes in the object being measured do not influence the distance measurements.

Thus, the neural network finds an approximation for a relation which cannot be solved in mathematically closed manner. However, it is not simple to extract the approximation from the trained connection weights. Tests with different input values and network structures furnish experimental statements on solubility and necessary minimal requirements of also similar problems.

As regards advantageous embodiments of the sensor arrangement in accordance with the invention, as well as the method of the present invention for the detection of measured values with this sensor arrangement, which have not be considered in the foregoing description of the Figures, the general description of the invention is herewith incorporated by reference.

Finally, it should expressly be remarked one more time that the sensor arrangement of the present invention may be used not only for measuring distance and thickness, but also for measuring material parameters, such as electric conductivity and effective permeability.

I claim:

1. Method of processing and evaluating measured signals within a sensor arrangement (1) so as to determine an actual value associated with a characteristic of an object to be measured, the sensor arrangement being of the type including at least one measuring coil (2), at least one voltage source (3), and an evaluation unit (4) with means for detecting, processing, and evaluating the measured signals, the evaluation unit (4) for evaluating the measured signals including a neural network (5) with a plurality of nodes arranged into an input layer, at least one hidden layer, and an output layer, and connection weights for the nodes of the individual layers, the connection weights being determined and stored during a learning phase by making measurements on a plurality of different suitable learning objects each with a known actual value and iteratively determining the connection weights required to produce said known actual values as outputs from the network, the method comprising the steps of:

biasing the measuring coil with an energizing voltage comprising several frequency components;

detecting a voltage curve $U_x$ and a current flow $I_x$ on the measuring coil (2) simultaneously at said several frequencies;

digitizing the voltage curve $U_x$ and the current flow $I_x$; and determining spectra of the digitized voltage curve $U_x$ and the digitized current flow $I_x$ in an iterative operation with the aid of a spectral estimator as $$x_{n+1}\text{HfL} := x_n\text{HfL}\left\{\frac{1}{kn+1}\sum x_p e^{\frac{a\pi T}{T_0}N} + \left[1 - \frac{1}{k} \cdot \frac{1}{kn+1}\right] x_n\text{HfL}\right\}$$

where $x_n(t)$ is the sampling value at the time n, $X_n(f)$ the spectrum at the time n, and $X_{n+}(f)$ the newly calculated spectrum at the time n+1, that the term $aT/T_0$ is used to select the desired spectral line, and n=0 and $X_0(f)=0$ are selected as starting values of the iteration, such that the determination of the spectra results in determination of at least as many nonlinear dependent but physicomathematically connected input values as there are input nodes.

2. Method as in claim 1, characterized in that from the voltage curve $U_x$ and current flow $I_x$ the impedance values of the measuring coil (2) are determined at different frequencies for use as input values for the neural network (5).

3. Method as in claim 1, characterized in that the measuring coil (2) is energized with a square-wave voltage.

4. Method as in claim 3, characterized in that the square-wave voltage is formed by a periodically recurrent sequence of respectively one square pulse of a larger amplitude and three square pulses of a smaller amplitude.

5. Method as in claim 1, characterized in that the energizing voltage of the measuring coil (2) comprises aside from an alternating current component also a direct current component.

6. Method as in claim 5, characterized in that the purely ohmic component of the impedance values of the measuring coil (2) forms an input value for the neural network (5).

7. Sensor arrangement, comprising at least one measuring coil, at least one voltage source for the measuring coil, and an evaluation unit with means for detecting, processing, and evaluating measured signals, the evaluation unit for evaluating the measured signals including a neural network having a plurality of nodes arranged into an input layer, at least one hidden layer, and an output layer, and connection weights for the nodes of the individual layers, the connection weights being determined and stored during a learning phase by making measurements on a plurality of different suitable learning objects each with a known actual value and iteratively determining connection weights required to produce the known actual values as outputs of the network, the voltage source being followed by a mixer arrangement which generates an energizing voltage signal containing several components of different amplitudes and frequencies, whereby the measuring coil is simultaneously energized by the several components of different frequencies, and the sensor arrangement further including means for detecting an output voltage curve $U_x$ from the measuring coil, and a spectral estimator operable for determining spectra of the voltage curve $U_x$ which spectra are used as inputs to the input layer of the neural network.

8. Sensor arrangement as in claim 7, characterized in that the evaluation unit (4) comprises a four-wire-type circuit arrangement with a current branch for detecting the voltage curve $U_x$ and a current branch for detecting the current flow $I_x$ of the measuring coil (2).

9. Sensor arrangement as in claim 7, characterized in that the evaluation unit comprises means for digitizing (7), for carrying out a Fourier analysis (8), for complex dividing (9), and for normalizing and scaling the measured signals (10), and that these means (7, 8, 9, 10) for processing the measured signals precede the neural network (5).

10. Sensor arrangement as in claim 7, characterized in that the neural network (5) is a back-propagation network.

11. Sensor arrangement as in claim 7, characterized in that the neural network (5) has a single-stage network structure, i.e., a network structure with one hidden layer.

12. Sensor arrangement as in claim 11, characterized in that the input layer of the neural network (5) comprises eight, six, four, or two input nodes.

13. Sensor arrangement as in claim 11, characterized in that the hidden layer of the neural network (5) comprises five, four, two nodes, or one node.

14. Sensor arrangement as in claim 7, characterized in that the neural network has a two-stage network structure with two hidden layers.

15. Sensor arrangement as in claim 7, characterized in that the output layer of the neural network (5) comprises one output node.

16. Sensor arrangement as in claim 7, characterized in that a sigmoid function adapted to the nonlinearity behavior of the measuring coil (2) and having a strictly monotonic and differentiable curve, is used as transfer function of the neural network.

17. Use of a method according to claim 1 for measuring a distance to and a coating thickness of said object to be measured.

18. Use of a method according to claim 1 for measuring an electric conductivity of and an effective relative permeability of said object to be measured.

* * * * *

UNITED STATES PATENT AND TRADEMARK OFFICE
CERTIFICATE OF CORRECTION

PATENT NO. : 5,898,304
DATED : April 27, 1999
INVENTOR(S) : Mandl

It is certified that error appears in the above-identified patent and that said Letters Patent is hereby corrected as shown below:

Column 7, line 34, "$X_{N+}(f)$" should read --$X_{N+1}(f)$--.

Signed and Sealed this

Fourteenth Day of September, 1999

Attest:

Q. TODD DICKINSON

*Attesting Officer*     *Acting Commissioner of Patents and Trademarks*